United States Patent
Bert et al.

(10) Patent No.: US 9,861,835 B2
(45) Date of Patent: Jan. 9, 2018

(54) METHOD FOR DETERMINING A DOSE ENTERING AN OBJECT THAT IS TO BE IRRADIATED

(71) Applicants: Christoph Bert, Uttenreuth (DE); Robert Luechtenborg, Muenster (DE)

(72) Inventors: Christoph Bert, Uttenreuth (DE); Robert Luechtenborg, Muenster (DE)

(73) Assignee: GSI HELMHOLTZZENTRUM FUER SCHWERIONENFORSCHUNG GMBH, Darmstadt (DE)

( * ) Notice: Subject to any disclaimer, the term of this patent is extended or adjusted under 35 U.S.C. 154(b) by 820 days.

(21) Appl. No.: 14/357,577

(22) PCT Filed: Dec. 3, 2012

(86) PCT No.: PCT/EP2012/074223
§ 371 (c)(1),
(2) Date: May 12, 2014

(87) PCT Pub. No.: WO2013/092181
PCT Pub. Date: Jun. 27, 2013

(65) Prior Publication Data
US 2014/0324402 A1    Oct. 30, 2014

(30) Foreign Application Priority Data
Dec. 22, 2011 (DE) ........................ 10 2011 056 882

(51) Int. Cl.
*G06G 7/48* (2006.01)
*A61N 5/10* (2006.01)

(52) U.S. Cl.
CPC ......... *A61N 5/1031* (2013.01); *A61N 5/1049* (2013.01); *A61N 5/1067* (2013.01);
(Continued)

(58) Field of Classification Search
CPC .............................................. A61N 2005/1089
(Continued)

(56) References Cited

U.S. PATENT DOCUMENTS

2010/0301235 A1   12/2010   Bert et al.
2012/0238795 A1   9/2012    Bert et al.

FOREIGN PATENT DOCUMENTS

DE   102009055902 A1   6/2011
JP   2010540050 A      12/2010
WO   WO 2011153639 A2  12/2011

OTHER PUBLICATIONS

Engelsman et al.: Target volume dose considerations in proton beam treatment planning for lung tumors; Med. Phys. 32 (12). Dec. 2005; pp. 3549-3557.*

(Continued)

*Primary Examiner* — Hugh Jones
(74) *Attorney, Agent, or Firm* — Leydig, Voit & Mayer, Ltd.

(57) ABSTRACT

A method for determining a dose of radiation input into an object irradiated with an energetic particle beam includes determining, during the application of the radiation, a dose input into at least one volume region of the object. The at least one volume region of the object lies outside a target volume region. The dose input into the at least one volume region is determined with a calculation that is based at least in part on a physical model of the energetic particle beam.

16 Claims, 4 Drawing Sheets

(52) U.S. Cl.
CPC .... *A61N 5/1043* (2013.01); *A61N 2005/1087* (2013.01); *A61N 2005/1089* (2013.01)

(58) Field of Classification Search
USPC .......................................................... 703/6
See application file for complete search history.

(56) References Cited

OTHER PUBLICATIONS

Kraemer, et al., "Treatment planning for heavy-ion radiotherapy: physical beam model and dose optimization", Phys. Med. Biol. 45 (2000), Nov. 1, 2000, pp. 3299-3317.

\* cited by examiner

METHOD FOR DETERMINING A DOSE ENTERING AN OBJECT THAT IS TO BE IRRADIATED

CROSS-REFERENCE TO RELATED APPLICATIONS

This application is a U.S. National Phase application under 35 U.S.C. §371 of International Application No. PCT/EP2012/074223 (WO 2013/092181 A1), filed on Dec. 3, 2012 and claims benefit to German Patent Application No. DE 10 2011 056 882.4, filed Dec. 22, 2011.

FIELD

The invention relates to a method for determining the radiation dose input into an object, which is to be irradiated with an energetic particle beam. The invention further relates to a treatment monitoring system and to an irradiation system.

BACKGROUND

The use of radiation of various types and energies for charging, for machining workpieces to be machined, or for altering material properties of workpieces to be machined has become widespread in the art for a wide range of fields of application.

In this context, photon radiation (in other words in particular charging with light, charging with X-ray radiation, UV light, infra-red light and the like) is not the only possible type of radiation; in particular, particle radiation may also be considered. In this context, the particles may be substantially as desired ("particles" in this context meaning in particular particles which have a rest mass, even though it may be extremely small). Hadrons and leptons may be mentioned purely by way of example, in particular including neutrinos, electrons, positrons, pions, mesons, protons, neutrons, atomic nuclei (for example He nuclei), atoms or molecules and ions (in particular including heavy ions such as oxygen ions, helium ions, neon ions or carbon ions).

What all these types of radiation have in common is that the radiation deposits a particular energy in the item charged with radiation. However, in some cases the manner in which this energy is deposited varies greatly. Whilst for example in the case of photon radiation the energy loss is related approximately exponentially to the material penetrated over wide energy ranges, particle beams, in this case in particular hadron particles (especially protons, ions and heavy ions), have a pronounced Bragg peak. The particles thus initially lose comparatively little energy on the path thereof upon penetrating material. Shortly before the particles come to rest, the majority of the energy is released into the material charged with the radiation. As a result of this Bragg peak, not only two-dimensionally structured dose charges, but in particular also three-dimensionally structured dose charges can be realised (in other words different deposited radiation doses at different depths in the irradiated object).

Not only may the type of radiation used vary, but so also may the type of objects charged with radiation. To name just a few technical fields of application, possible examples relating to charging with protons in structuring processes include masks and material removal or material application in the manufacture of structured semiconductor components (such as memory elements, microprocessors and the like).

Photons may also be used for cutting and/or welding workpieces (in particular if the photon radiation is in the form of a high-energy laser beam).

One example application for electron beams is electron beam welding, by means of which for example two metal workpieces can be welded together. Naturally, separation and structuring processes are also conceivable.

In medicine and veterinary medicine, radiation is used for therapeutic purposes. For example, it is known to use X-ray radiation for producing X-ray images (including three-dimensional images from CT (computed tomography) methods). Electron beams have also been used in medicine for several decades, for example for treating cancerous tumours. Treatment of tumours using protons and ions (in particular heavy ions) has also now become well established in medicine. Because of the previously described Bragg peaks of protons/ions/heavy ions, it is possible to charge a three-dimensionally defined and structured region (in particular a tumour) in a patient with radiation in a targeted manner by controlling a particle beam accordingly (for example as part of a scanning process), whilst the surrounding tissue is largely unaffected. Precisions in the millimeter range are now possible.

In scanning methods, a thin particle beam (often referred to as a pencil-thin particle beam) is conventionally used, and can be deflected laterally (x-y plane) using suitable deflection magnets and controlled in terms of penetration depth using suitable energy variation. By varying deflection and energy accordingly, it is possible to "approach" the various volume regions to be charged with a dose of the object to be irradiated. Irradiation generally follows a radiation treatment plan. In this context, a particular radiation pattern is computer-simulated (in other words a sequence with different x-y deflections of the particle beam and suitable particle energies of the particle beam) and the respectively resulting dose input into the body charged with the radiation is calculated as a function of location. This is because, although the deposited dose in the irradiated object is concentrated on the region of the Bragg peak, a particular dose is nevertheless deposited (in particular in regions lying close to the radiation point along the particle path). In the context of the radiation treatment plan, attempts are made to optimise the particle beam guidance in such a way that there is charging with a particular minimum dose within a region to be treated (usually referred to as the CTV (clinical target volume)) of the object. By contrast, surrounding material (tissue) should be exposed to as low a dose as possible.

Particular problems occur if (sub-regions of) the object to be irradiated move. In this context, movement may include not only translational movements, but also twisting movements and/or compression or extension movements. In particular in combination with scanning methods, the movements of the object and those of the particle beam may "interfere" with one another and lead to comparatively poor radiation results if suitable countermeasures are not taken.

A method which has now become widespread so as to be able to irradiate moving target regions involves tracking the particle beam. In this context, the particle beam is readjusted in such a way that it compensates the movement of the target volume region in the object. With beam tracking of this type, it is in fact possible for the matrix dot which is actually to be irradiated (or the target radiation position and/or the target volume region) to be controlled substantially with the planned dose. However, because the movements in the object to be irradiated cannot be predicted during planning (in particular in combination with the movements of the particle beam), dose inputs which cannot be planned in advance occur in regions which do not correspond to the matrix point currently being irradiated. As a result of the accumulation of doses introduced outside the currently controlled matrix dot in the material, the doses introduced during an object machining process (or a therapy session) can lead to a very significant difference between the target plan and the dose distribution actually introduced.

It is therefore desirable to measure the movement of the object during the irradiation of said object, and, by using these measurements, to calculate what the actual dose distribution in the irradiated object is. Knowledge of this type can also be used for example within the object machining process (for example in that the radiation yet to follow is adapted accordingly), or else at a later time, in particular if the entirety of the machining is carried out in a plurality of object machining sessions separated in time.

Methods by which dose input monitoring of this type can be carried out have been proposed.

For example, German Offenlegungsschrift DE 10 2009 055 902 A1 has proposed a method in which a compensation value for the $i^{th}$ matrix position is calculated as a function of the determined dose which the $i^{th}$ matrix position has already received when irradiating the previous matrix positions, and a compensated particle flow for the $i^{th}$ matrix position is calculated as a function of the compensation value for the $i^{th}$ matrix position and of the nominal particle flow for the $i^{th}$ matrix position, so as to irradiate the $i^{th}$ matrix position with the compensated particle flow determined for the $i^{th}$ matrix position. The difference between the target dose and the actual dose in the $i^{th}$ matrix position is determined using a pre-calculated database for dose compensation, in matrix form, having a large number of individual field elements $D_m^{ik}$. The dose compensation proposed therein delivers fully usable results. However, experience has shown that application in practice is limited to very small volumes where the number of matrix positions is relatively small. For larger volumes (CTV sizes above approximately 10 cm$^3$), however, the storage requirement for storing the field elements increases excessively. Specifically, the storage requirement for the field elements increases proportionally to the square of the number of matrix positions. Thus, volumes above approximately 10 cm$^3$ result in storage requirements in the gigabyte range, and even with modern computers this can only be implemented with difficulty. Further, the time required for advance calculation of the field elements $D_m^{ik}$ increases disproportionately.

SUMMARY

In an embodiment, the present invention provides a method for determining a dose input into an object to be irradiated with an energetic particle beam. The method includes determining, during the an application of radiation into the object, a dose input into at least one volume region of the object lying outside a target volume region via, the dose input being determined using a calculation based at least in part on a physical model of the energetic particle beam.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION OF THE DRAWINGS

Figure 1:
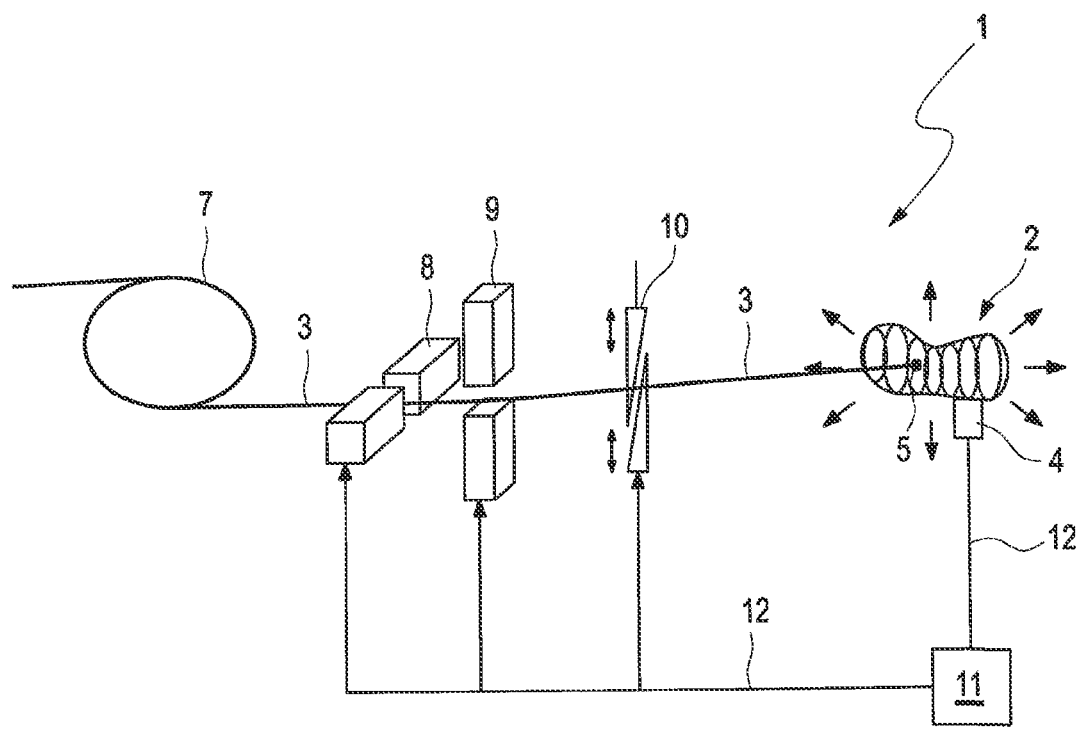
FIG. 1 is a schematic view of a conceivable device for applying an energetic particle beam.

An aspect of the invention provides a universally applicable method for determining the dose input in material regions lying outside the target volume region currently being irradiated. Another aspect provides an improved device for determining the dose input in volume regions lying outside the target volume region currently being irradiated.

It is proposed to carry out a method for determining the dose input into an object, which is to be irradiated with an energetic particle beam, during the application of the radiation, in which the dose input is determined, at least at times and/or at least in part, in volume regions lying outside the target volume region respectively irradiated by the energetic particle beam, in such a way that a calculation function based at least in part on a physical model of the energetic particle beam is used for determining the dose input. The energetic particle beam is preferably a thin (pencil-thin) particle beam, which is preferably moved during the application of the radiation. This may involve movement methods known in technical language as scanning methods (in particular raster scanning methods, spot scanning methods or continuous scanning methods). The particle beam may in particular consist of particles which have a rest mass (even though it may be small). In particular, they may be hadrons, in particular protons, helium nuclei, ions, heavy ions (in particular oxygen ions, carbon ions, neon ions), and possibly also the non-ionised equivalents thereof. However, in principle it is also possible for an unmoved particle beam to be used and/or for the particle beam to be widened using suitable measures. Further, leptons (in particular electrons and positrons) are also conceivable as particles. The object may in principle be any desired object. This may in particular be a workpiece to be machined, such as a semiconductor material, a metal material or the like. In particular, however, it is also conceivable for these to be objects from the medical field. In this context, however, these need not necessarily be human and animal patients, but may also include cell cultures and irradiation phantoms, in particular, which can be used for example to verify a previously calculated radiation treatment plan before it is actually used for treatment. Although charged particle radiation (in particular hadron radiation) generally has a pronounced Bragg peak, it is nevertheless unavoidable that a certain dose will also be introduced into regions not actually "approached" by the particle beam. This applies in particular to volume regions lying close to the currently controlled target volume region. It should be noted that in the present application the term "target volume region" generally means the direct vicinity of the Bragg peak (although in some cases this term may also refer to the target volume marked out by the doctor, such as the tumour to be irradiated). Since the doses introduced in this manner may accumulate over time, and the resulting dose inputs cannot be planned in advance, in particular in the presence of movements of the object to be irradiated, it is expedient to determine these dose inputs during the actual application of the radiation, in particular in order that they can be taken into account at a later time, although this may still be during the current application session. It should be noted that this "undesired dose input" may make up a very significant proportion of the dose input in a particular volume region, and in particular fluctuations caused by movements may lead to major deviations from the dose calculated and adopted in the radiation treatment plan. The inventors have found that when calculating this dose input it is expedient to use a calculation function based at least in part on a physical model of the energetic particle beam. To their own surprise, it was thus possible to reduce the storage requirement quite considerably in the case of larger volume regions to be irradiated. In particular, in a first trial using tens of thousands of matrix dots, it was possible to reduce the necessary storage requirement from one gigabyte to just under one megabyte. Further, the storage requirement of the method proposed herein only scales linearly (and no longer quadratically as for example in the method proposed in DE 10 2009 055 902 A1), and so even very large objects can reasonably be irradiated. This is presumably possible because in the previous methods, in the pre-calculation of the transmission coefficients, there is a large redundancy (not needed per se) between individual matrix values. However, by using physical models, symmetries and the like for example may advantageously be exploited, resulting in major advantages, in particular in relation to the storage requirement. As stated above, this means that large objects can now for the first time be made accessible to irradiation (which is movement-compensated and/or adaptive) in practice.

In the method, it is further proposed for the dose input to be determined at least at times and/or at least in part in volume regions which correspond to the target volume region irradiated by the energetic particle beam. This does not merely make it possible to monitor a dose input in volume regions lying "alongside the currently controlled matrix point". Rather, it is also possible to monitor the dose introduced in the currently controlled target volume region. As a result, any fluctuations and/or unanticipated effects can also be detected therein, and this can generally lead to an improvement in the irradiation or to an improvement in the irradiation monitoring.

In the method, it has been found to be expedient if the physical model of the particle beam is based on a substantially Gaussian distribution of the particle beam profile. Measurements have demonstrated that an assumption of this type generally matches actual particle beam profiles in a good to excellent approximation. Accordingly, first trials have demonstrated that the results which can ultimately be achieved using the proposed method are particularly good. For completeness, it should be noted that the Gaussian distribution can be adopted not only for (substantially) circular particle beam profiles, but also for example for elliptical or oval particle beam profiles.

In the method, it is further advantageous if the physical model is based on an energy loss model upon passing through material. This generally corresponds to the actual data, in particular of hadron particle beams upon passing through material. Using the model, the effects inherent to such particle types, such as in particular the non-linear energy loss upon passing though material as a function of the density of the material and/or of the (rest) energy of the particles (highly non-linear, in particular in the region of the Bragg peak), can also be taken into account in these particle types. The energy model can be "transformed" into a corresponding calculation function using integration methods known per se.

If the object to be irradiated moves at least at times and/or at least in regions during the application of the irradiation, in particular moves in itself, and preferentially at least sub-regions of the object to be irradiated carry out translational movements and/or rotational movements and/or expansion or compression movements, the proposed method can particularly advantageously be used. In particular, if movements of this type are present, this can result in particularly large deviations of the doses introduced in volume regions outside the matrix dot currently being irradiated with respect to a target plan. In particular in relation to translational movements and/or rotational movements, it should be noted that movements of this type can lead to displacement of material regions of different densities in the particle beam direction. Accordingly, the effective depth of the particle beam may also vary and/or the distribution type of the deposited energy in material regions along the particle beam may vary greatly. Extension or compression movements generally also lead to changes in density in the object to be irradiated, in such a way that in this case too particularly strong effects in the dose deposition can result in regions outside the current matrix dot. However, if these dose deposition effects are taken into account, in particular by using the proposed method, the overall treatment success can generally be improved considerably.

It is particularly advantageous if the movement of at least parts of the object to be irradiated is determined. In this context, the movement may be detected or at least approximated using imaging methods (for example methods using X-ray radiation, ultrasound methods and the like), using objects to be followed (for example implanted gold balls or other marker substances) and/or using movement substitutes. A movement substitute is for example an expansion measurement strip which is placed around a patient's ribcage. Prior to the actual irradiation, a correlation between movement state and extension of the expansion measurement strip can be detected, for example by using imaging methods. If the length of the expansion measurement strip is determined during the actual treatment, a conclusion as to the current movement state can be inferred in a good approximation.

In the method, it is particularly advantageous if the energetic particle beam compensates the movement of the object to be irradiated, at least at times and/or at least in regions. This may in particular be understood within the meaning of tracking methods. In particular, it is possible for the lateral position of the particle beam to be provided using a corresponding deflection system (for example a deflection magnet) and/or for energy adaptation of the particles, and thus adaptation of the penetration depth of the particle beam into the object, to be provided. In this way, it is at least possible for the "current matrix dot" substantially to match the plans. However, it is noted that the proposed compensation movement may also relate to tracking the particle beam trajectory (meaning that there can also be a direct influence on the irradiation input into volume regions which do not match the matrix dot volume region currently being controlled). This can be provided by moving the particle beam itself (for example by using a gantry) and/or for example by moving a treatment couch.

In the proposed method, it is particularly advantageous if the dose input determined during the application of the radiation has an influence on the subsequent irradiation. In this way, the determined values (in particular deviations from previous adopted values) can be "used expediently". Subsequent irradiation may refer on the one hand to online adaptation, meaning that adaptation can be provided even during the current material-machining session (treatment session). However, this may also involve a plurality of material-machining sessions (treatment sessions) separated in time and, by means of the obtained data, for example an radiation treatment plan to be determined for a subsequent treatment session can accordingly be suitably adapted whilst taking into account the data thus obtained. The dose introduced can be adapted in particular by changing the number of particles introduced. In particular, the number of particles introduced can be changed by changing the resting time of a particle beam in a particular beam position. A longer resting time usually results in a higher particle input (and a shorter resting time accordingly results in a lower particle input). In addition or alternatively, however, it is also possible for example for an accelerator device to be readjusted accordingly so as to change the particle flow.

In the method, it is further advantageous if the dose inputs determined during the application of the radiation are stored and/or outputted. In particular, this makes it possible to archive the obtained data and use them again later. This may relate not only to subsequent object-machining sessions, but also for example to evidence preservation measures, research projects and the like.

In the method, it is possible for the physical model to be present as an analytical function and/or as a table of values at least at times and/or at least in part. An analytical representation may in particular further reduce the storage requirement for storing the data. By contrast, a table of values may be found to be advantageous if the analytical function is comparatively complex, meaning that an analytical calculation, in particular online, would require too much computation time. Naturally, a combination method is also conceivable, in such a way that for example an analytical calculation is undertaken in the x-y direction and a table of values is used for the z direction. A combination between the two extremes is also conceivable and generally also expedient, for example within the meaning that a table of values is interpolated (linear, spline and the like).

It is further advantageous if the energetic particle beam is moved during the application of the radiation, in particular in the manner of scanning, preferably in the manner of raster scanning, spot scanning and/or continuous scanning. As a result, it is particularly advantageously possible to introduce dose input fields of substantially any desired shape into an object (an object region). The method can be used particularly advantageously and/or can deliver particularly advantageous results in an application of this type.

In the method, it is further proposed to determine a difference between a target dose and an actually applied dose. These deviations can in particular be taken into account at a later time (especially including during the current dose application/radiation fraction). In particular, a dose input into a particular target volume region (matrix dot or beam position, sometimes also referred to in laboratory jargon as a voxel, albeit not entirely correctly) can be reduced or increased in accordance with the value determined in this manner if it is currently being "approached" by the particle beam.

A treatment monitoring system comprising at least one monitoring device is further proposed, in which the monitoring device is formed and set up in such a way that it comprises a method of the above-disclosed type. The treatment monitoring system can thus comprise the aforementioned properties and advantages in an at least analogous manner. Further, the treatment monitoring system can be developed within the meaning of the preceding description, at least analogously.

An irradiation system is further proposed, which comprises at least a treatment monitoring system of this type. In this case too, it is possible for the radiation system to comprise the properties and advantages proposed above analogously and/or to be developed within the meaning of the preceding description, at least analogously.

FIG. 1 is a schematic drawing of an irradiation device 1 for irradiating an object 2 with a high-energy particle beam 3 (in this case heavy ions). In this context, the irradiation device 1 is simultaneously formed and set up in such a way that a movement of the object 2 (indicated by arrows) can be measured by means of a movement substitution measurement sensor 4 (for example an expansion measurement strip which is laid around the ribcage of a patient), so as to determine the dose input not only in the beam position 5 currently being irradiated, but also in other volume regions (positions 6), in particular in positions 14, 15 located close to the current beam position 5 as seen in the particle beam direction 3. In this context, in laboratory jargon the beam position 5 currently being irradiated is sometimes, not entirely correctly, referred to as a target voxel, and the (other) positions 6, 14, 15 are accordingly referred to as voxels.

The irradiation device 1 comprises an accelerator, which in the present case is formed as a synchrotron 7 (a linear accelerator (linac) generally being provided upstream, but not being shown in FIG. 1 for reasons of clarity). The ion source for generating the ions in the particle beam 3 is also not shown in FIG. 1 for reasons of clarity.

The highly accelerated particle beam 3 which leaves the synchrotron 7 is deflected by two deflection coil pairs 8, 9 in the horizontal (deflection coil pair 8) and vertical (deflection coil pair 9) directions. In the particle beam 3, (rapid) energy variation is possible by way of two absorber wedges 10 (energy variation device) which can be displaced with respect to one another. By means of the deflection coil pairs 8, 9 and the absorber wedges 10, a target volume located inside the object 2 to be irradiated can be scanned by approaching a large number of beam positions 5, and thus can be allocated a specific dose. Simultaneously, by means of the deflection coil pairs 8, 9 and the absorber wedges 10, the moving beam position 5 inside the object 2 can be tracked using the data of the movement substitute measurement sensor 4, and the movement of the respective beam position 5 can thus be substantially compensated. The data of the movement substitute measurement sensor 4 are processed by an electronic computer 11, which is supplied with data via corresponding data lines 12 and which outputs corresponding control commands to the deflection coil pairs 8, 9 and the absorber wedges 10.

Naturally, it is possible for the electronic computer 11 also to process other, further data. Moreover, the electronic computer 11 may optionally also send data to the synchrotron 7 (and/or other regions of the accelerator), so as for example to bring about greater energy variations (in particular greater energy variations than can be represented using the absorber wedges 10). However, an energy variation of the synchrotron 7 can conventionally only be implemented from one particle spill to the other, and thus requires a comparatively long time, making it expedient to use absorber wedges 10 (or another rapid energy variation device).

Before applying the radiation, a radiation treatment plan calculated in advance is read into the electronic computer 11. Since the movements of the object 2 (in particular internal movements of the object 2) cannot be predicted in the context of the radiation treatment plan, it is necessary to measure the movement of the object 2 during the actual application of the radiation, both so as to be able to carry out tracking and so as to be able to determine the dose input into volume regions outside the actual (current) beam position 5.

Figure 2:
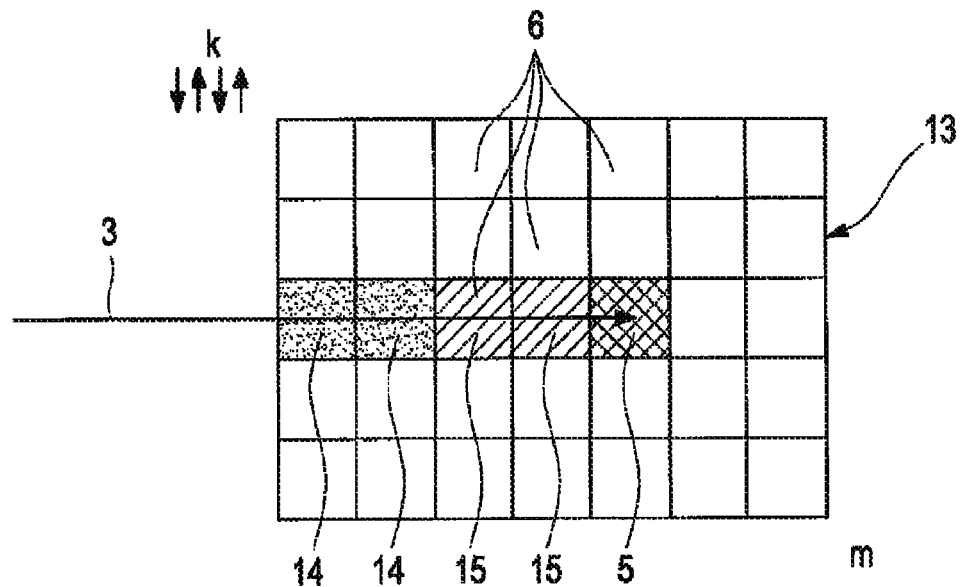
FIG. 2 is an example sketch illustrating the influence of the dose distribution in tissue regions lying close to a target point in the presence of movement of the target object.
Figure 2:
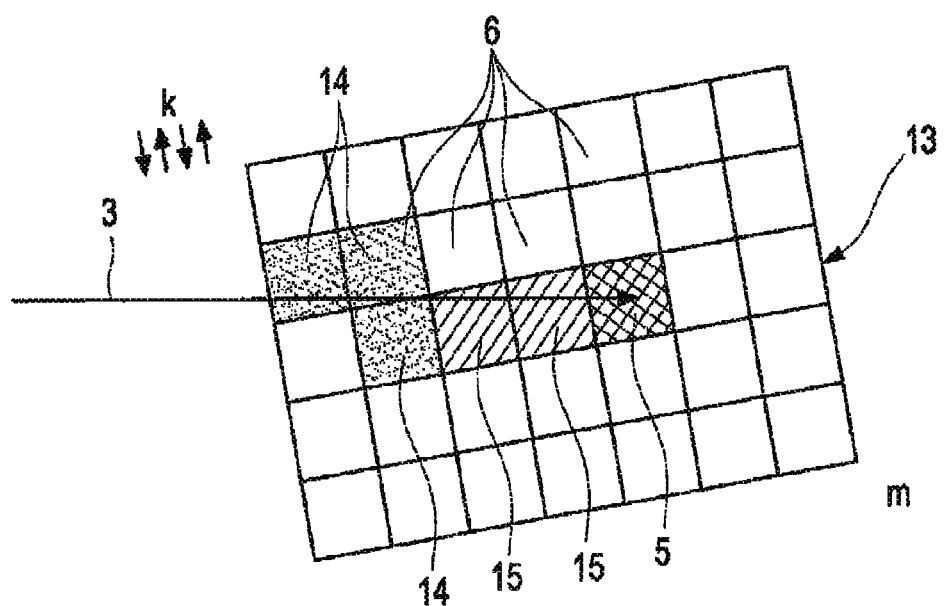

By way of illustration, FIG. 2 shows schematically the effects brought about by a movement of an object 2 in terms of the dose deposition in different positions 6, in particular in positions 14, 15 close to the actual beam position 5. FIG. 2 shows a detail 13 of an object 2 to be irradiated in each case. The detail 13 is subdivided into a number of individual finite, controllable volume regions, referred to herein as positions 6. FIG. 2 further shows the incident particle beam 3. Since herein the detail 13 is selected in such a way (sufficiently small) that all of the positions 5 are approached by the particle beam 3 at a particular time, all of the positions 6 are radiation positions 5 at a particular radiation time. Further, by contrast, positions 6 lying outside the detail 13 are (in part) not approached by the particle beam 3. Nevertheless, these positions 6 are also taken into account in determining the dose input respectively "unintentionally" introduced into them. As a result of the movement of the object 2 (or parts of the object 2), the detail 13 moves, in such a way that the position grid 6 is correspondingly displaced and twisted. Simple displacement (translational displacement) of the detail 13 can generally be compensated well by suitable deflection and energy adaptation of the particle beam 3 (corresponding control of the deflection coil pairs 8, 9 and the absorber wedges 10). However, a rotational movement, such as occurs between FIG. 2a (movement state m') and FIG. 2b (movement state m), generally cannot be compensated in this way. As can be seen from the two sub-drawings of FIG. 2, twisting the detail 13 in this manner results in the particle beam 3 now penetrating other positions 6, even though the same beam position 5 is controlled. In this context, by way of illustration, the correspondingly penetrated positions 6 (in other words the positions 14, 15 close to the beam position 5) are subdivided herein into positions 14 in which there is weak energy deposition (dotted) and positions 15 in which there is a medium energy deposition (hashed). The primary region of the Bragg peak is in the beam position 5 provided with a cross pattern, and so there is very strong energy deposition here.

As stated previously, the dose input into the positions 6 other than the actual beam position 5 (in particular into the positions 14, 15) can only be determined during the actual irradiation of the object 2, since the movements of the object 2 are not known when the radiation treatment plan is drawn up. Previously, a matrix describing a mapping function from a dose input into a beam position 5 (the scanning process meaning that the beam position 5 also changes over the course of irradiation) and the other positions 6 was used for calculating the relevant dose proportions. In this context, the coefficients of this matrix have to be determined in advance for each individual movement phase which may realistically be expected during the irradiation. The storage requirement of the corresponding matrix increases approximately quadratically with the number of positions 6 to be taken into account. Therefore, even for comparatively small target areas of a few square centimeters, a storage requirement of several gigabytes is needed just for the matrix. Since this needs to be RAM (otherwise online calculation would not be possible, since for example hard disk access takes too much time), even currently available computers rapidly come up against technical limitations.

Accordingly, it is proposed to use a calculation function based on a physical model of the particle beam, instead of a matrix filled with coefficients, to calculate the dose inputs into the different positions 6.

Figure 3:
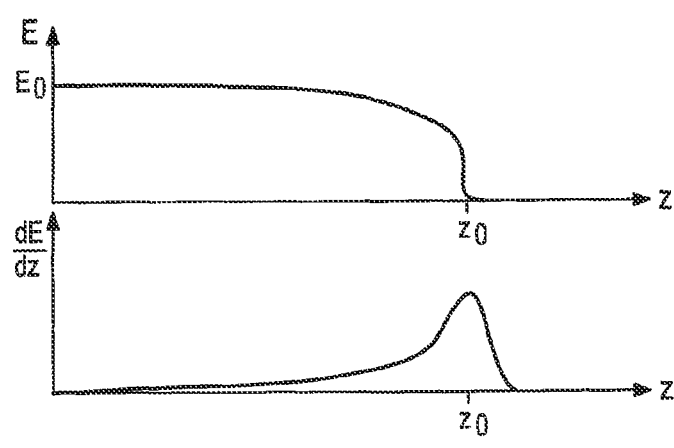
FIG. 3 shows a possible example of physical assumptions for a physical model of an energetic particle beam.
Figure 3:
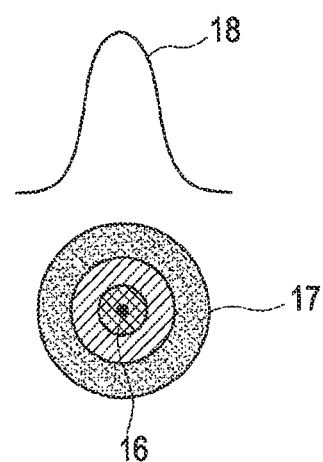

One conceivable physical model which can be used to generate the calculation function is sketched in FIG. 3. In this context, FIG. 3a shows the model in the propagation direction of the particle beam 3 (z direction), whilst FIG. 3b shows the lateral extension of the particle beam.

In FIG. 3a, an upper diagram shows the energy E as a function of the material penetrated (length z). In this context, an arbitrarily selected starting energy value $E_0$ is assumed. In the helium ion beam used herein as a particle beam, there is initially a comparatively low energy loss. Only shortly before the maximum of the Bragg peak at $z_0$ does the energy start to decrease strongly, achieving a maximum gradient in the region of the Bragg peak maximum $z_0$. The relationships are clarified further in the lower diagram of FIG. 3a, where the differential energy loss per unit length dE/dz (and thus the dose input per unit volume) is plotted against the material penetrated in the z direction.

FIG. 3b further shows a particle beam 3 having a Gauss-like intensity distribution about the midpoint 16 of the particle beam diameter 16. A Gauss curve 18 is shown in the upper region. To clarify the relationships, a plurality of concentric circles of different intensities are drawn about the midpoint 16 of the particle beam diameter 17 (although in reality the particle intensities usually decrease continuously in accordance with the Gauss curve 18, and not stepwise).

On the basis of this mathematical model, the following relationship is obtained as a possible function for the transformation function $D(E_{beam}, r, z)$:

$$D(E_{beam}, r, z)[Gy] = \qquad (1)$$
$$1.6 \cdot 10^{-8} d(E_{beam}, z) \left[\frac{\text{MeVcm}^2}{g}\right] \frac{N}{2\pi\sigma\sigma^2[\text{mm}^2]} \exp\left(-\frac{r^2}{2\sigma^2}\right)$$

In this context, the function $D(E_{beam}, r, z)$ is a relationship describing the dose input as a function of the penetration depth z, and is explained in greater detail in the following. N is the particle count, σ is the standard deviation of the particle beam width, and r is the distance from the midpoint 16 of the particle beam diameter 17.

The Relationship:

$$d(E_{beam}, z) = \frac{\sum_T \int_E dE \frac{dN}{dE}(E_{beam}, z, T, E)(dE)}{\rho dx}(T, E) \qquad (2)$$

can be used for the function $d(E_{beam}, z)$, and is derived for example in the scientific publication "Treatment planning for heavy-ion radiotherapy: physical beam model and dose optimization" by M. Krämer, O Jaeckel, T. Haberer, G. Kraft, D. Schardt and U. Weber in Phys. Med. Biol. 45 (2000) 3299-3317. In this context, dN/dE is the differential energy spectrum for an individual differential isoenergy disc. T is a measure of the specific particle species, which is defined by the atomic number Z and the atomic mass A. ρ stands for the density of the penetrated material.

Therefore, using the stated relationships, for each individual irradiated beam position 5 (which is denoted for example by a particular index i), the dose input into another position 6, which is provided for example with the index k, in a movement phase m can be calculated. By taking the difference between the actual radiation input calculated in this manner and the radiation input in the radiation treatment plan, the correction value $\Delta d_{m(i)}^{ik}$ is obtained from the relationship:

$$\Delta d_{m(i)}^{ik} = \qquad (3)$$
$$D_{norm}(E^i, r_m^k, z_m^k)\Big|_{\vec{x}_m^i + \Delta \vec{x}_m^i} \cdot N_{adapt}^i - D_{norm}(E^i, r_{ref}^k, z_{ref})\Big|_{\vec{x}_m^i} \cdot N_{Nom}^i$$

where the following holds for $D_{norm}(E^i, r_m^k, z_m^k)$:

$$D_{norm}(E_{beam}, r, z)[Gy] = \qquad (4)$$
$$1.6 \cdot 10^{-8} d(E_{beam}, z)\left[\frac{\text{MeV cm}^2}{g}\right]\frac{1}{2\pi\sigma^2[\text{mm}^2]}\exp\left(-\frac{r^2}{2\sigma^2}\right)$$

Formula (4) is therefore the above formula (1) with "1" substituted for the particle count "N", and this is thus a standardised function (standardised by way of example to a particle count of "1").

Subsequently, in formula (3), scaling to the particle count $N_{adapt}^i$, which is unknown prior to the actual irradiation and generally varies itself as a result of the dose compensation being used, is carried out.

$r_m^k$ is the radial distance of the position k in the movement phase m with respect to the beam position $\vec{x}_m^i$ during irradiation of the position i in the movement phase m using the tracking parameter $\Delta \vec{x}_m^i$ ("displacement" of the particle beam 3), whilst $x_m^k$ is the water equivalent depth of the position k in the movement phase m with respect to the beam position $\vec{x}_m^i$ during irradiation of the position I in the movement phase m using the tracking parameter $\Delta \vec{x}_m^i$.

In the context of the radiation proportions yet to be applied, the correction value $\Delta d_{m(i)}^{ik}$ can be taken into account when irradiating a corresponding beam position 5. This can take place for example by altering the dwell time (shorter or longer) of the particle beam at the relevant beam position 5. It is likewise possible for the data "merely" to be stored and for example taken into account for calculating a radiation treatment plan for an irradiation fraction still to be applied.

Figure 4:
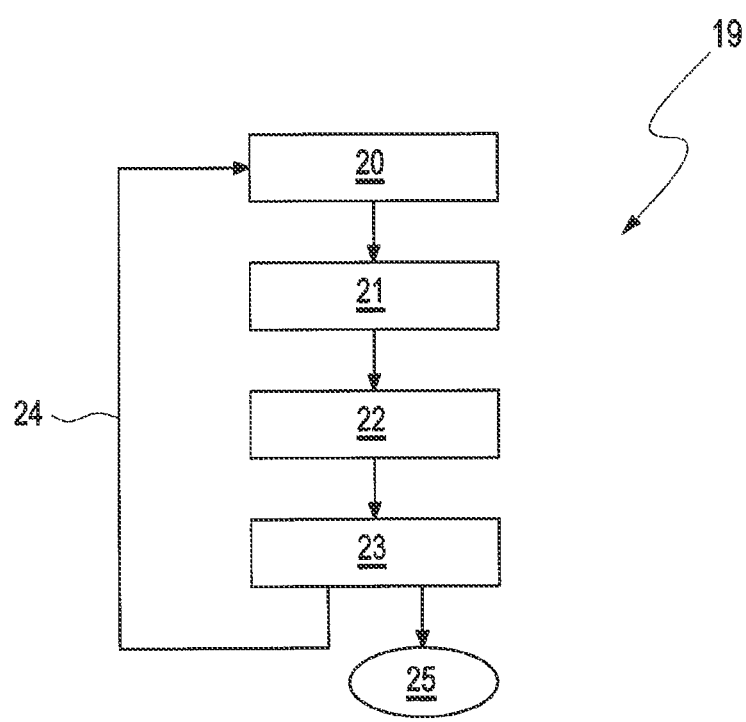
FIG. 4 shows a possible method for determining the dose input into an object in different volume regions.

Finally, FIG. 4 further schematically shows a flow chart 19 for the method proposed herein. In a first step 20, the current movement phase 20 is detected (for example using the measurement from a movement substitute measurement sensor 4). On this basis, in a following step 21 the dose inputs into the different positions 6 are calculated (in particular into the beam position 5 and into positions 14, 15 close to the beam position 5). This makes use of a function which has been determined using a physical model, for example using the formulae (1) to (4) explained above.

Subsequently, in a step 22, the difference between the planned target dose and the actually applied dose 22 is determined. The difference values 22 determined in this manner are used in a correction step 23 so as to adapt the particle input into target voxels 6 which are yet to be irradiated, even during the current irradiation fraction (correction both "upwards" and "downwards" being possible).

Subsequently, there is a jump 24 to the start of the method 19, as long as the irradiation has not yet been fully applied. By contrast, if the irradiation has been carried out in its entirety, the method stops (branch 25). In conjunction with this step, the dose values may also additionally be stored and for example outputted onto a storage medium, in such a way that they can be taken into account in subsequent irradiation fractions in the radiation treatment plan respectively to be calculated for this purpose.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE NUMERALS 1 irradiation device
2 object
3 particle beam
4 movement substitute measurement sensor
5 beam position
6 position
7 synchrotron
8 deflection coil pair, horizontal
9 deflection coil pair, vertical
10 absorber wedges
11 electronic computer
12 data line
13 detail of the object
14 weak deposition
15 medium deposition
16 midpoint
17 particle beam diameter
18 Gauss curve
19 flow diagram
20 determine movement phase
21 determine dose inputs
22 determine difference
23 correction step 24 jump back
25 stop

The invention claimed is:

1. A method for applying radiation into an object with an energetic particle beam, the method comprising:
    obtaining a radiation treatment plan calculated in advance of application of radiation into the object to be irradiated;
    applying radiation into the object to be irradiated at a first beam position according to the radiation treatment plan;
    during the applying radiation into the object to be irradiated, determining, using a calculation based at least in part on a physical model of the energetic particle beam, an actual radiation dose input into at least one outside volume region of the object lying outside a target volume region;
    determining a difference between the actual radiation dose input into the at least one outside volume region and a planned radiation dose input into the at least one outside volume region according to the radiation treatment plan; and
    obtaining, based on the difference, a correction value that can be taken into account during applying radiation into the object to be irradiated at subsequent beam positions.

2. The method of claim 1, further comprising:
    determining, during the applying radiation into the object to be irradiated at the first beam position, a dose input into at least one volume region of the object lying inside the target volume region.

3. The method of claim 1, wherein the physical model of the energetic particle beam is based on a substantially Gaussian distribution of the particle beam profile.

4. The method of claim 1, wherein the physical model of the energetic particle beam is based on an energy loss model upon passing through the material.

5. The method of claim 1, wherein, during at least a portion of time during which the application of radiation into the object to be irradiated occurs, a movement occurs of at least one of the object to be irradiated and a region of the object to be irradiated.

6. The method of claim 5, wherein the movement is at least one of a translational movement, a rotational movement, an expansion movement, or a contraction movement.

7. The method of claim 1, further comprising detecting a movement of at least a part of the object being irradiated.

8. The method of claim 7, wherein the energetic particle beam compensates for the movement that occurs.

9. The method of claim 1, wherein the correction value has an influence on subsequent radiation.

10. The method of claim 1, further comprising at least one of:
    storing data indicating the determined actual radiation dose input into the at least one outside volume region, or
    outputting data indicating the determined actual radiation dose input into the at least one outside volume region.

11. The method of claim 1, wherein at least a portion of the physical model of the energetic particle beam is an analytical function.

12. The method of claim 1, wherein at least a portion of the physical model of the energetic particle beam is a table of values.

13. The method of claim 1, further comprising moving the energetic particle beam during the application of radiation into the object to be irradiated from the first beam position to one or more of the subsequent beam positions.

14. The method of claim 13, wherein the movement of the energetic particle beam is at least one of raster scanning, spot scanning, or continuous scanning.

15. A system for determining a dose of radiation input into an object to be irradiated with an energetic particle beam, the system comprising:
    at least one monitoring device configured to:
        determine, during an application of radiation into the object at a first beam position according to a radiation treatment plan calculated in advance of the application of radiation into the object, an actual radiation dose input into at least one outside volume region of the object lying outside a target volume region, wherein the actual radiation dose input into the at least one outside volume region is determined using a calculation based at least in part on a physical model of the energetic particle beam;
        determine a difference between the actual radiation dose input into the at least one outside volume region and a planned radiation dose input into the at least one outside volume region according to the radiation treatment plan; and
        obtain, based on the difference, a correction value that can be taken into account during application of radiation into the object at subsequent beam positions.

16. A system for irradiating an object with an energetic particle beam, the system comprising:
    at least one monitoring device configured to:
        determine, during an application of radiation into the object at a first beam position according to a radiation treatment plan calculated in advance of the application of radiation into the object, an actual radiation dose input into at least one outside volume region of the object lying outside a target volume region, wherein the actual radiation dose input into the at least one outside volume region is determined using a calculation based at least in part on a physical model of the energetic particle beam;
        determine a difference between the actual radiation dose input into the at least one outside volume region and a planned radiation dose input into the at least one outside volume region according to the radiation treatment plan; and
        obtain, based on the difference, a correction value that can be taken into account during application of radiation into the object at subsequent beam positions.

* * * * *